(12) United States Patent
D'Amato et al.

(10) Patent No.: US 7,291,610 B2
(45) Date of Patent: *Nov. 6, 2007

(54) ESTROGENIC COMPOUNDS AS ANTI-MITOTIC AGENTS

(75) Inventors: Robert John D'Amato, Lancaster, PA (US); Moses Judah Folkman, Brookline, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/402,386

(22) Filed: Apr. 12, 2006

(65) Prior Publication Data

US 2006/0183727 A1 Aug. 17, 2006

Related U.S. Application Data

(60) Continuation of application No. 09/780,650, filed on Feb. 12, 2001, now Pat. No. 7,109,187, which is a continuation of application No. 09/436,610, filed on Nov. 9, 1999, now abandoned, which is a continuation of application No. 09/243,158, filed on Feb. 2, 1999, now Pat. No. 6,528,676, which is a division of application No. 08/838,699, filed on Apr. 25, 1997, now Pat. No. 5,892,069, which is a division of application No. 08/571,265, filed on Dec. 12, 1995, now Pat. No. 5,661,143, which is a continuation of application No. 08/102,767, filed on Aug. 6, 1993, now Pat. No. 5,504,074.

(51) Int. Cl.
   *A61K 31/56* (2006.01)
(52) U.S. Cl. .................................................. 514/182
(58) Field of Classification Search ................ 514/182
   See application file for complete search history.

(56) References Cited

U.S. PATENT DOCUMENTS

| | | | |
|---|---|---|---|
| 2,584,271 A | 2/1952 | Huffman | |
| 2,846,453 A | 8/1958 | Hoehn | |
| 3,166,577 A | 1/1965 | Ringold et al. | |
| 3,410,879 A | 11/1968 | Smith et al. | |
| 3,470,218 A | 9/1969 | Farah | |
| 3,492,321 A | 1/1970 | Crabbe | |
| 3,496,272 A | 2/1970 | Kruger | |
| 3,562,260 A | 2/1971 | De Ruggieri et al. | |
| 3,950,437 A | 4/1976 | Imamura et al. | |
| 3,956,348 A | 5/1976 | Hilscher | |
| 4,172,132 A | 10/1979 | Draper et al. | |
| 4,212,864 A | 7/1980 | Tax | |
| 4,307,086 A | 12/1981 | Tax | |
| 4,444,767 A | 4/1984 | Torelli et al. | |
| 4,522,758 A | 6/1985 | Ward et al. | |
| 4,552,758 A | 11/1985 | Murphy et al. | |
| 4,634,705 A | 1/1987 | DeBernardis et al. | |
| 4,743,597 A | 5/1988 | Javitt et al. | |
| 4,808,402 A | 2/1989 | Leibovich et al. | |
| 4,994,443 A | 2/1991 | Folkman et al. | |
| 5,001,116 A | 3/1991 | Folkman et al. | |
| 5,135,919 A | 8/1992 | Folkman et al. | |
| 5,504,074 A | 4/1996 | D'Amato et al. | |
| 5,621,124 A | 4/1997 | Seilz et al. | |
| 5,643,900 A | 7/1997 | Fotsis et al. | |
| 5,661,143 A | 8/1997 | D'Amato et al. | |
| 5,750,576 A * | 5/1998 | DeGregorio et al. | ........ 514/720 |
| 5,892,069 A | 4/1999 | D'Amato et al. | |
| 5,919,459 A | 7/1999 | Nacy et al. | |
| 6,011,023 A | 1/2000 | Clark et al. | |
| 6,011,024 A | 1/2000 | Reed et al. | |
| 6,528,676 B1 | 3/2003 | D'Amato et al. | |
| 6,723,858 B2 | 4/2004 | D'Amato et al. | |
| 6,908,910 B2 | 6/2005 | D'Amato et al. | |
| 6,930,128 B2 | 8/2005 | D'Amato et al. | |
| 2002/0165212 A1 | 11/2002 | D'Amato et al. | |
| 2003/0096800 A1 | 5/2003 | D'Amato et al. | |
| 2004/0072813 A1 | 4/2004 | D'Amato et al. | |

FOREIGN PATENT DOCUMENTS

| | | |
|---|---|---|
| DE | 1907330 | 10/1969 |
| DE | 3625315 | 1/1988 |
| EP | 0166937 A2 | 8/1986 |
| GB | 857080 | 12/1960 |
| GB | 857081 | 12/1960 |
| GB | 1570597 | 7/1980 |
| GB | 2252498 A | 8/1992 |
| JP | 39-5480 B | 3/1961 |
| JP | 41 000100 A | 1/1966 |
| JP | 42-928 B | 1/1967 |
| JP | 62-135472 | 6/1987 |
| JP | 63090763 A | 4/1988 |
| JP | 63-119500 | 5/1988 |
| JP | 04-046120 | 2/1992 |
| WO | WO 87/02367 A3 | 4/1987 |
| WO | WO 88/03151 A2 | 5/1988 |
| WO | WO 88/08002 A1 | 10/1988 |
| WO | WO 90/15816 A1 | 12/1990 |
| WO | WO 93/03729 A1 | 3/1993 |
| WO | WO 93/10805 A1 | 6/1993 |

(Continued)

OTHER PUBLICATIONS

Seegers et al., "The cytotoxic effects of estradiol-17beta, catecholestradiols and methoxyestradiols on dividing MCF-7 and HeLa cells." J. Steroid Biochem., vol. 32(6), pp. 797-809, 1989.*

(Continued)

*Primary Examiner*—Barbara P. Badio
(74) *Attorney, Agent, or Firm*—King & Spalding LLP

(57) ABSTRACT

The application discloses methods of treating mammalian diseases characterized by abnormal cell mitosis by administering estradiol derivatives including those comprising colchicine or combretastatin A-4 structural motifs of the general formulae found below in a dosage sufficient to inhibit cell mitosis. The application discloses novel compounds used in the methods.

12 Claims, 3 Drawing Sheets

FOREIGN PATENT DOCUMENTS

| WO | WO 93/19746 A1 | 10/1993 |
|---|---|---|
| WO | WO 95/04535 A1 | 2/1995 |

OTHER PUBLICATIONS

Schumacher et al., "The physiological estrogen metabolite 2-methoxyestradiol reduces tumor growth and induces apoptosis in human solid tumors." J. Cancer Res. Clin. Oncol., vol. 127, pp. 405-410, 2001.*
Pribluda et al., "2-Methoxyestradiol: An endogenous antiangiogenic and antiproliferative drug candidate." Cancer and Metastasis Reviews, vol. 19, pp. 173-179, 2000.*
Hori, A. et al., Suppression of Solid Tumor Growth by Immunoneutralizing Monoclonal Antibody Against Human Basic Fibroblasts Growth Factor, *Cancer Research*, vol./Iss:51, pp. 6180-6184, Date: Nov. 15, 1991.
Kim, K.J. et al., Inhibition of Vascular Endothelial Growth Factor-induced Angiogenesis Suppresses Tumor Growth In Vivo, *Nature*, vol./Iss:362, pp. 841-844, Date: Apr. 29, 1993.
Yang, Ning-Sun, Gene Transfer into Mammalian Somatic Cells/l Vivo, *Critical Reviews in Biotechnology*, vol./Iss:12(4), pp. 335-356, Date: 1992.
U.S. Appl. No. 09/644,387, filed Aug. 23, 2000.
U.S. Appl. No. 11/235,574, filed Sep. 26, 2005.
U.S. Appl. No. 11/347,880, filed Feb. 6, 2006.
U.S. Appl. No. 09/939,208, filed Aug. 24, 2001.
U.S. Appl. No. 11/118,852, filed Apr. 29, 2005.
U.S. Appl. No. 10/856,340, filed May 28, 2004.
U.S. Appl. No. 10/918,627, filed Aug. 12, 2004.
U.S. Appl. No. 11/230,375, filed May 19, 2005.
U.S. Appl. No. 10/789,471, filed Feb. 27, 2004.
U.S. Appl. No. 11/077,977, filed Mar. 11, 2005.
U.S. Appl. No. 11/288,989, filed Nov. 29, 2005.
Lilopristone/(1-[4-(Dimethylamino)phenyl]-17-hydroxy-17-(3-hydroxy-1-propenyl) estra-4,9-diene-3-one; AK 98734, *Dictionary of Drugs (1990), Dict. of Steroids (1991), Dict. of Org. Cmpds (6th Ed) (1996), Dict. of Pharm Agents(1997)*, Date: 1990.
(Paragraphs 583-584), *The Merck Index 11th Edition*, pp. 88, Date: 1989.
*Research Plus Catalog*, pp. 50-58, Date: 1993.
Aboulwafa et al., Synthesis and evaluation for uterotrophic and antiimplantation activities of 2-substituted estradiol derivatives, *Steroids*, vol./Iss: 57, pp. 199-204, Date: Apr. 1992.
Adams, E.F. et al., Steroidal regulation of oestradiol-17B dehydrogenase activity of the human breast cancer cell line MCF-7 (Chemical Abstracts Doc No. 109:32325, 1988), *Journal of Endocrinology*, vol./Iss: 118(1), pp. 149-154, Date: Jul. 1988.
Algire, G.H. et al., Title:Vascular reactions of normal and malignant tumors in vivo. I. Vascular reactions of mice to wounds and to normal and neoplastic transplants, *Journal of the National Cancer Institute*, vol./Iss: 6, pp. 73-85, Date: Aug. 1945.
Aliev et al., 54929q Synthesis of cycloalkyl derivatives of dihydric phenols and their ethers, *Chemical Abstracts*, vol./Iss: 72, pp. 370, Date: 1970.
Banik et al., Orally Active Long-Acting Estrogen (AY-20,121) (3-(2-propynyloxy)-estra-1,3,5,(10)-triene-17. beta.-ol trimethylacetate) (Identifier only), *Steroids*, vol./Iss: 16(3), pp. 289-296, Date: 1970.
Bardon et al., Steroid Receptor-Mediated Cytotoxicity of an Antiestrogen and an Antiprogestin in Breast Cancer Cells (Abstract only), *Cancer Research*, vol./Iss:47 (5), pp. 1441-1448, Date: Mar. 1, 1987.
Barnes et al., Tumor Necrosis Factor Production in Patients with Leprosy, *Infection and Immunity*, vol./Iss:60 (4), pp. 1441-1446, Date: Apr. 1992.
Bhat et al., Estradiol-induced Mitotic Inhibition in the Bursa of Fabricius of Male Domestic Duckling (Chemical Abstracts Doc. No. 98:31837, 1982), *Mikroskopie*, vol./Iss:39, pp. 113-117, Date: May 1982.
Bhattacharyya et al., Tubulin aggregation and disaggregation: Mediation by two distinct vinblastine-binding sites, *National Academy of Sciences*, vol./Iss:73 (7), pp. 2375-2378, Date: Jul. 1976.

Bindra et al., Studies in Antifertility Agents.8.Seco Steroids. 2. 5,6-Secoestradiol and Some Related Compounds, *Journal of Medicinal Chemistry*, vol./Iss:18 (9), pp. 921-925, Date: 1975.
Blickenstaff et al., Estrogen-Catharanthus (Vinca) Alkaloid Conjugates (Chemical Abstracts Doc. No. 94:114277, 1981), *Cytotoxic Estrogens in Hormone Receptive Tumors*, pp. 89-105, Date: 1980.
Blickenstaff et al., Synthesis of Some Analogs of Estradiol, *Steroids*, vol./Iss:46 (4,5), pp. 889-902, Date: Oct. 1985.
Boyce et al., Some Preliminary Synthetical Studies with 5,6,7,8-Tetra-hydro-8-methylindane-1,5-dione, *Unknown*, pp. 4547-4553, Date: 1960.
Boye et al., 185. Deaminocolchinyl Methyl Ether: Synthesis from 2,3,4,4'-Tetramethoxybiphenyl- 2-carbaldehyde. Comparison of Antitubulin Effects of Deaminocolchinyl Methyl Ether and Dehydro Analogs, *Helvetica Chimica Acta*, vol./Iss:72, pp. 1690-1696, Date: 1989.
Brandi et al., Bone endothelial cells as estrogen targets (Abstract only), *Calcif. Tissue Int.*, vol./Iss:53 (5), pp. 312-317, Date: 1993.
Brem, H. et al., Interstitial chemotherapy with drug polymer implants for the treatment of recurrent gliomas, *Journal of Neurosurgery*, vol./Iss:74, pp. 441-446, Date: Mar. 1, 1991.
Brosens et al., Comparative Study of the Estrogenic Effect of Ethinylestradiol and Mestranol on the Endometrium, *Contracteption, (Laboratory for Gynecological Physiopathology)*, vol./Iss:14 (6), pp. 679-685, Date: Dec. 1, 1976.
Cambie et al., Aromatic Steroids. Part II. Chromium Trioxide Oxidation of Some Oestra-1,3-5(10)-trienes, *Journal of the Chemical Society*, vol./Iss:9, pp. 1234-1240, Date: 1969.
Cambie et al., Aromatic Steroids. Part I. Oxidation Products of 3-Methoxyestra-1,3,5(10)-triene- 17β-yl Acetate, *J. Chem. Soc.*, pp. 2603-2608, Date: 1968.
Castagnetta, L. et al., Simple Approach to Measure Metabolic Pathways of Steroids in Living Cells, *Journal of Chromatography*, vol./Iss:572, pp. 25-39, Date: Dec. 6, 1991.
Chasserot-Golaz et al., Biotransformation of 17.beta.-hydroxy-11. beta.-(4-dimethylaminophenyl)17.alpha.1-propynyl-estra-4,9-diene-3-one (RU486) in Rat Hepatoma Variants (Identifier only), *Biochemical Pharmacology*, vol./Iss:46 (11), pp. 2100-2103, Date: 1993.
Chen et al., A New Synthetic Route to 2- and 4-Methoxyestradiols by Nucleophilic Subsitution, *Steroids*, vol./Iss:47 (1), pp. 63-66, Date: Jan. 1986.
Chen et al., Synthesis of 11.beta.-(4-dimethylaminophenyl)-17. beta-hydroxy-17.alpha.-(1-propynyl) estra-4,9-dien-3-one (RU486) (Identifier only), *Nanjing Yaoxueyuan Xuebao* vol./Iss:17 (4), pp. 282-285, Date: 1986.
Cohen et al., Novel Total Synthesis of (+)-Estrone 3-Methyl Ether, (+)-13βEthyl-3-methoxygona-1,3,5(10)-trien-17-one, and (+)-Equilenin 3-Methyl Ether, *The Journal of Organic Chemistry*, vol./Iss:40 (6), pp. 681-685, Date: Mar. 21, 1975.
Collins et al., The Structure and Function of Estrogens. XI. Synthesis of (+/−)-7(8-11α) abeo-Estradiol and its 9,11-Didehydro Derivative, *Aust. Journal of Chemistry*, vol./Iss:45 (1), pp. 71-97, Date: 1992.
Corey et al., Applications of N,N-Dimethylhydrazones to Synthesis. Use in Efficient, Positionally and Stereochemically Selective C-C Bond Formation; Oxidative Hydrolysis to Carbonyl Compounds, *Tetrahedron Letters*, vol./Iss:1, pp. 3-6, Date: 1976.
Corey et al., Facile Conversion of N,N-Dimethylhydrazones to Cabonyl Compounds by Cupric Ion-Catalyzed Hydrolysis, *Tetrahedron Letters*, vol./Iss:41, pp. 3678-3668, Date: 1976.
Crabbe, P., Cotton effect of the styrene chromophore (Abstract only), *Chem. Ind.*, vol./Iss:27, pp. 917-918, Date: 1969.
Crum, R. et al., A New Class of Steroids Inhibits Angiogenesis in the Presence of Heparin or a Heparin Fragment, *Science*, vol./Iss:230, pp. 1375-1378, Date: Dec. 20, 1985.
Durani et al., Seco-Oestradiols and Some Non-Steroidal Oestsrogens: Structural Correlates of Oestrogenic Action, *Journal of Steroid Biochemistry*, vol./Iss:11, pp. 67-77, Date: 1979.
DVIR et al., Thin-layer Chromatography of DANSYL-oestrogens, *Journal of Chromatography*, vol./Iss:52, pp. 505-506, Date: Nov. 4, 1970.

Eder et al., Synthese von Ostradiol (in German—No translation available) English Abstract only, *Chem. Ber.*, vol./Iss:109, pp. 2948-2953, Date: 1976.

Emons et al., Modulation der hypophysaren Sekretion von Luteinisierendem Hormon (LH) durch Ostrogene English Abstract only, *FOCUS MHL*, vol./Iss:3, pp. 221-228, Date: 1986.

Epe et al., Microtubular Proteins as Cellular Targets for Carcinogenic Estrogens and Other Carcinogens, *Mechanisms of Chromosome Distribution and Aneuploidy*, pp. 345-351, Date: 1989.

Evans et al., A Convergent Total Synthesis of +/− Colchicine and +/− Desacetamidoisocolchicine, *Journal of the American Chemical Society*, vol./Iss:103, pp. 5813-5821, Date: Sep. 23, 1981.

Fanchenko et al., Characterisitics of the guinea pig uterus estrogen receptor system (Abstract only), *Byull. Eksp. Biol. Med.*, vol./Iss:85 (4), pp. 467-470, Date: 1978.

Fetizon et al., Synthesis of 2-keto steroids (Abstract only), *Bull. Soc. Chim. FR.*, vol./Iss: 8, pp. 3301-3306, Date: 1968.

Fevig et al., A Short, Stereoselective Route to 16α-(Substituted-alkyl)estradiol Derivatives, *Journal of Organic Chemistry*, vol./Iss:52, pp. 247-251, Date: 1987.

Field et al., Effect of Thalidomide on the Graft versus Host Reaction, *Nature*, vol./Iss:211 (5055), pp. 1308-1310, Date: Sep. 17, 1966.

Fieser et al., N-Methylformanilide, *Organic Synthesis Collective vol. 3*, vol./Iss:3, pp. 590-591, Date: 1955.

Fishman, J., Synthesis of 2-Methoxyestrogens, *Journal of the American Chemical Society*, vol./Iss:80, pp. 1213-1216, Date: Mar. 5, 1958.

Fitzgerald, Molecular Features of Colchicine Associated with Antimitotic Activity and Inhibition of Tubulin Polymerization, *Biochemical Pharmacology*, vol./Iss:25 (12), pp. 1383-1387, Date: Jun. 15, 1976.

Flohe et al., Studies on the Hypothetical Relationship of Thalidomide-induced Embryopathy and Collagen Biosynthesis, *Arzneimitte/Forschung (Germany West)*, vol./Iss:31 (2), pp. 315-320, Date: Jan. 1, 1981.

Folkman et al., Angiogenesis Inhibition and Tumor Regression Caused by Heparin or a Heparin Fragment in the Presence of Cortisone, *Science*, vol./Iss:221, pp. 719-725, Date: Aug. 19, 1983.

Folkman, J., Tumor Angiogenesis: Therapeutic Implications, *New England Journal of Medicine*, vol./Iss:285 (21), pp. 1182-1186, Date: Nov. 18, 1971.

Folkman, J. et al., Induction of Angiogenesis During the Transition from Hyperplasia to Neoplasia, *Nature*, vol./Iss: 339, pp. 58-61, Date: May 4, 1989.

Folkman, J. et al., Tumor Behavior in Isolated Perfused Organs in vitro Growth and Metastases of Biopsy Material in Rabbit Thyroid and Canine Intestinal Segment, *Annals of Surgery*, vol./Iss: 164(3), pp. 491-502, Date: Sep. 1, 1966.

Gandhi et al., Mannich Reaction of Estrone Abstract only, *Journal of Indian Chem. Soc.*, vol./Iss:39, pp. 306-308, Date: 1962.

Gaslini et al., Reaction of Eugenol with Synthesis Gas. Synthesis of 5,6,7,8-Tetrahydro-3-methoxy-2-napthol, *Journal of Organic Chemistry*, vol./Iss:29 (5), pp. 1177-1180, Date: May 1964.

Getahun et al., Synthesis of Alkoxy-Substituted Diaryl Compounds and Correlation of Ring Separation with Inhibition of Tubulin Polymerization: Differential Enhancement of Inhibitory Effects Under Suboptimal Polymerization Reaction Conditions, *Journal of MedicinalChemistry*, vol./Iss:35 (6), pp. 1058-1067, Date: Mar. 20, 1992.

Gian Tondury et al., Zur Wirkung Der Sexualhormone Auf Wachstum und Differenzierung (See English Summary p. 55), *Cambridge Philosophical Society*, pp. 28-58, Date: Dec. 17, 1955.

Gimbrone, M.A. et al., Tumor Growth and Neovascularization: An Experimental Model Using the Rabbit Cornea, *Journal of the National Cancer Institute*, vol./Iss:52(2), pp. 413-427, Date: Feb. 1974.

Gimbrone, M.A. et al., Tumor dormancy in vivo by Prevention of Neovascularization, *Journal of Experimental Medicine*, vol./Iss: 136, pp. 261-276, Date: 1972.

Gonzalez et al., Synthesis and Pharmacological Evaluation of 8αEstradiol Derivatives, *Steroids*, vol./Iss:40 (2), pp. 171-187, Date: Sep. 1982.

Gross et al., Inhibition of Tumor Growth, Vascularization, and Collagenolysis in the Rabbit Cornea by Medroxyprogesterone, *Procedings of the National Academy of Science USA*, vol./Iss: 78 (2), pp. 1176-1180, Date: Feb. 1981.

Gross, J.L. et al., Modulation of Solid Tumor Growth in vivo by bFGF (Abstract only), *Proceedings of the American Association of Cancer Research*, vol./Iss:31, pp. 79, Date: Mar. 1990.

Gunzler, V., Thalidomide-A Therapy for the Immunological Consequences of HIV Infection,? *Medical Hypothesis*, vol./Iss:30 (2), pp. 105-109, Date: Oct. 1989.

Gupta et al., Antifertility Agents. XIV. Secosteroids. VII. Synthesis of 2αand 2β, 6β-dimethyl- 3β-(p-hyroxyphenyl)-trans-bicyclo[4.3.0]nonan-7-ones and some related compounds (Abstract only), *Indian Journal of Chemistry*, vol./Iss:13 (7), pp. 759-760, Date: 1975.

Gupta et al., Studies in Antifertility Agents. Part XVIII. 2α6β-Diethyl-3β-(p-hydroxyphenyl)-trans-bicyclo[4.3.0]nonan-7β-ol and 6β-methyl-3β(p-hydroxyphenyl)-2α-propyl- trans-bicyclo[4.3.0]nonan-7β-ol (Abstract only), *Indian Journal of Chemistry*, vol./Iss:19B (10), pp. 886-890, Date: 1980.

Gutierrez-Rodriguez, Treatment of Refractory Rheumatoid Arthritis—The Thalidomide Experience et al., *The Journal of Rheumatology*, vol./Iss:16 (2), pp. 158-163, Date: Feb. 1989.

Gutierrez-Rodriguez, Thalidomide—A Promising New Treatment for Rheumatoid Arthritis, *Arthritis and Rheumatism*, vol./Iss:27 (10), pp. 1118-1121, Date: Oct. 1984.

Hahnel et al., The Specificity of the Estrogen Receptor of Human Uterus, *Journal of Steroid Biochemistry*, vol./Iss: 4, pp. 21-31, Date: 1973.

Handley et al., Chronic bullous disease of childhood and ulcerative colitis, *British Journal of Dermatology*, vol./Iss:127 (40), pp. 67-68, Date: Jul. 1, 1992.

Hartley-Asp et al., Diethylstilbestrol Induces Metaphase Arrest and Inhibits Microtubule Assembly, *Mutation Research*, vol./Iss:143 (4), pp. 231-235, Date: Aug. 1985.

Heney et al., Thalidomide treatment for chronic graft-versus-host disease, *British Journal of Haematology*, vol./Iss:78 (1), pp. 23-27, Date: May 1991.

Himes et al., Action of the Vinca Alkaloids Vincristine, Vinblastine, and Desacetyl Vinblastine Amide on Microtubules in Vitro, *Cancer Research*, vol./Iss:36, pp. 3798-3802, Date: Oct. 1976.

Holden et al., Mitotic Arrest by Benzimidazole Analogs in Human Lymphocyte Cultures, *Environmental Mutagenesis*, vol./Iss:2, pp. 67-73, Date: 1980.

Holker et al., The Reactions of Estrogens with Benzeneseleninic Anhydride and Hexamethyldisilazane, *J. Chem. Soc. Perkin Trans.*, vol./Iss:I, pp. 1915-1918, Date: 1982.

Huber et al., Tubulin Binding of Conformationally Restricted Bis-Aryl Compounds, *Bioorganic & Medicinal Chemistry Letters*, vol./Iss:1 (5), pp. 243-246, Date: 1991.

Ingber, D. et al., Synthetic analogues of fumagillin that inhibit angiogenesis and suppress tumor growth, *Nature*, vol./Iss:348, pp. 555-557, Date: Dec. 6, 1990.

Iriarte et al., Steroids (XCIV). Synthesis of 2-methyl and 1,2-dimethyl estrogens (Abstract only), *Tetrahedron*, vol./Iss:3, pp. 28-36, Date: 1958.

Jhingran et al., Studies in Antifertility Agents—Part XLI: Secosteroids-x: Syntheses of Various Stereoisomers of (+−)-2,6β-diethyl-7α-ethynyl-3-(p-hydroxyphenyl)-trans-bicyclo [4.3.0) nonan-7β-ol, *Steroids*, vol./Iss: 42 (6), pp. 627-634, Date: 1983.

Kabarity et al., Further Investigations on the cytological effects of some contraceptives, *Mutation Research*, vol./Iss: 135, pp. 181-188, Date: 1984.

Karwat, Separation and Recovery of Hydrogen Sulfide from Hydrocarbon Mixture identifier only, *Caplus DE 1103310*, Date: Sep. 2, 1959.

Kelly et al., The Stimulation of Prostaglandin Production by Two Antiprogesterone Steroids in Human Endometrial Cells (Abstract only), *Journal of Clinical Endocrinology Metabolism*, vol./Iss:62 (6), pp. 1116-1123, Date: Jun. 1986.

Knighton, D. et al., Avascular and Vascular Phases of Tumour Growth in the Chick Embryo, *British Journal of Cancer*, vol./Iss:35, pp. 347-356, Date: 1977.

Kole et al., Studies in Antifertility Agents. 11. Secosteroids.5. Synthesis of 9,11-Secoestradiol, *Journal of Medicinal Chemistry*, vol./Iss:18 (7), pp. 765-766, Date: 1975.

Kovacs et al., Steroids. XXIII. Synthesis of 2- and 4-hydroxy and 2,4-dihydroxy derivatives of estrone and estradiol (Abstract only), *Acta Phys.Chem.*, vol./Iss: 19 (3), pp. 287-290, Date: 1973.

Lewis, Richard J., *Hawley's Condensed Chemical Dictionary*, pp. 577, Date: Jan. 1993.

Lewis, Richard J., *Hawley's Condensed Chemical Dictionary*, pp. 128-129, Date: Jan. 1993.

Li, J., et al., (DN 103:65176) Catechol Formation of Fluoro- and Bromo-substituted Estradiols by Hamster Liver Microsomes. Evidence for Dehalogenation. (Abstract only), *CAPLUS: Molecular Pharmacology*, vol./Iss: 27 (5), pp. 559-565, Date: 1985.

Lien, W. et al., The blood supply of experimental liver metastases. II. A Microcirculatory study of the normal and tumor vessels of the liver with the use of perfused silicone rubber, *Surgery*, vol./Iss: 68 (2), pp. 334-340, Date: Aug. 1970.

Limantsev et al., Effect of some estrogen structural analogs on the development of the mouse embyo (Abstract only), *Akush Jinekol.*, vol./Iss: 6, pp. 55-56, Date: 1982.

Lin et al., Interactions of Tubulin with Potent Natural and Synthetic Analogs of the Antimitotic Agent Combretastatin: A Structure-Activity Study, *Molecular Pharmacology*, vol./Iss: 34 (2), pp. 200-208, Date: Aug. 1988.

Lincoln et al., Conformation of Thiocolchicine and Two B-Ring-Modified Analogues Bound to Tubulin Studied with Optical Spectroscopy, *Biochemistry*, vol./Iss: 30 (5), pp. 1179-1187, Date: Feb. 5, 1991.

Liu et al., Total Synthesis of (+−) -D***Capnellene, *Tetrahedron Letters*, vol./Iss: 26 (40), pp. 4847-4850, Date: 1985.

Loozen et al., An approach to the synthesis of 7.beta.-amino estrogens (Abstract only), *Recl.: J.R. Neth.Chem. Soc.*, vol./Iss: 102 (10), pp. 433-437, Date: 1983.

Lottering et al., Effects of the 17β-Estradiol Metabolites on Cell Cycle Events in MCF-7 Cells (Chemical Abstracts Doc. No. 117:245769, 1992), *Cancer Research*, vol./Iss: 52, pp. 5926-5932, Date: Nov. 1, 1992.

Luo et al., Effect of Components of Crowth Ether Copper(I)Iodide Mixed Catalyst on Nucleophilic Substitution of Bromoestrogen (Abstract No. 195225), *Chemical Abstracts*, vol./Iss: 111 (21), pp. 818, Column 1, Date: Nov. 20, 1989.

Manfredi et al., Taxol: An Antimitotic Agent with a New Mechanism of Action, *Pharmacology & Therapeutics*, vol./Iss:25 (1), pp. 83-125, Date: 1984.

Maro et al., Mechanism of Polar Body Formation in the Mouse Oocyte: An Interaction Between the Chromosomes, the Cytoskeleton and the Plasma Membrane, *Journal of Embryology and Experimental Morphology*, vol./Iss: 92, pp. 11-32, Date: 1986.

Maro et al., Changes in Actin Distribution During Fertilization of the Mouse Egg, *Journal of Embyology and Experimental Morphology*, vol./Iss: 81, pp. 211-237, Date: 1984.

Mayol et al., Ethynylestradiol-Induced Cell Proliferation in Rat Liver Involvement of Specific Populations of Hepatocytes (Abstract only), *Carcinogenesis*, vol./Iss:13 (12), pp. 2381-2388, Date: 1992.

Michel et al., Inhibition of synaptosomal high-affinity uptake of dopamine and serotonin by estrogen agonists and antagonists (Abstract only), *Biochem. Pharmacol.*, vol./Iss:36 (19), pp. 3175-3180, Date: 1987.

Morgan et al., Calcium and Oestrogen Interactions upon the Rat Thymic Lymphocyte Plasma Membrane (Chemical Abstracts Doc. No. 85:172052, 1976), *Biochemical and Biophysical Research Communications*, vol./Iss:72 (2), pp. 663-672, Date: Sep. 20, 1976.

Morisaki et al., Steroids. LI. Aromatization reaction of the cross-conjugated dienone system by Zinc 9. (Abstract only), *Chem. Pharm. Bull.*, vol./Iss: 14 (8), pp. 866-872, Date: 1966.

Mukundan et al., Liver Regeneration in Oral Contraceptive Treated Female Rats—Effects of Moderate Malnutrition (Chemical Abstracts Doc. No. 102:143342, 1984), *Hormone and Metabolic Research*, vol./Iss: 16 (12), pp. 641-645, Date: Dec. 1984.

Naafs et al., Thalidomide Therapy An Open Trial, *International Journal of Dermatology*, vol./Iss: 24 (2), pp. 131-134, Date: Mar. 1985.

Nakamura et al., Studies on the Total Synthesis of dHColchiceine. I. Synthesis of 3-Hydroxy-9, 10, 11-trimethoxy-1,2,3,4,6,7-hexahydro-5H-dibenzo[a,c] cycloheptatrien-5-one, *Chemical and Pharmaceutical Bulletin*, vol./Iss: 10, pp. 281-290, Date: 1962.

Nambara et al., Studies on Steroid Conjugates. III. New Synthesis of 2-Methoxyestrogens, *Chem. Pharm. Bulletin*, vol./Iss: 18 (3), pp. 474-480, Date: Mar. 1970.

Nambara et al., Microbial transformation products derived from steroids. I. Synthesis of 1,2- and 3-dimethoxy-4-methylestratrienes (Abstract only), *Chem. Pharm. Bull.*, vol./Iss:20 (2), pp. 336-342, Date: 1972.

Nambara et al., Synthesis of 16β-Oxygenated Catechol Estrogen Methyl Ethers, New and Potential Metabolites, *Chemical & Pharmaceutical Bulletin*, vol./Iss:23 (7), pp. 1613-1616, Date: Jul. 1975.

Nambara, T., et al., DN 82:43650; Analytical Chemical Studies on Steroids. LXXIII. Synthesis of Epimeric 2-Hydroxy-16-Chlorestrong Monomethyl Ethers (Abstract only), *HCAPLUS—Chemical and Pharmaceutical Bulletin*, vol./Iss:22 (10), pp. 2455-2457, Date: 1974.

Newkome et al., Synthesis of Simple Hydrazones of Carbonyl Compounds by an Exchange Reaction, *Journal of Organic Chemistry*, vol./Iss: 31, pp. 677-681, Date: Mar. 1966.

Nguyen, M. et al., Elevated Levels of the Angiogenic Peptide Basic Fibroblast Growth Factor in Urine of Bladder Cancer Patients, *Journal of the National Cancer Institute*, vol./Iss: 85 (3), pp. 241-242, Date: Feb. 3, 1993.

Numazawa et al., Efficient Synthesis of 2-Methoxy- and 4-Methoxy-Estrogens, *Journal of the Chemical Society*, pp. 533-534, Date: Jan. 1, 1983.

Numazawa et al., Novel and Regiospecific Synthesis of 2-Amino Estrogens via Zincke Nitration, *Steroids*, vol./Iss: 41 (5), pp. 675-682, Date: 1983.

Ochs et al., Effect of Tumor Promoting Contraceptive Steroids on Growth and Drug Metabolizing Enzymes in Rat Liver (Abstract only), *Cancer Research*, vol./Iss: 46 (3), pp. 1224-1232, Date: 1986.

Oppolzer et al., 177. The Enantioselective Synthesis of (+)-Estradiol from 1,3-Dihydrobenzo[c]thiophene-2,2-dioxide by Successive Thermal SO₂-Extrusion and Cycloaddition Reactions, *Helvetica Chimica Acta*, vol./Iss: 63, pp. 1703-1705, Date: 1980.

Paull et al., Identification of Novel Antimitotic Agents Acting at the Tubulin Level by Computer-assisted Evaluation of Differential Cytotoxicity Data, *Cancer Research*, vol./Iss:52 (14), pp. 3892-3900, Date: Jul. 15, 1992.

Pert et al., Preparations of 2,4-disubstituted estradiols (Abstract only), *Australian Journal of Chemistry*, vol./Iss:42 (3), pp. 421-432, Date: 1989.

Peters et al., 17-Desoxy Estrogen Analogues, *Journal of Medicinal Chemistry*, vol./Iss: 32 (7), pp. 1642-1652, Date: 1989.

Pfeiffer et al., Are catechol estrogens obligatory mediators of estrogen action in the central nervous system? I. Characterization of pharmacological probes with different receptor binding affinities and catechol estrogen formation rates (Abstract only), *Journal of Endocrinology*, vol./Iss:110 (3), pp. 489-497, Date: 1986.

Poli et al., Tumor Necrosis Factor α Functions in an Autocrine Manner in the Induction of Human Immunodeficiency Virus Expression, *Proceedings of the National Academy of Science USA*, vol./Iss:87 (2), pp. 782-785, Date: Jan. 1990.

Powell et al., Investigation and Treatment of Orogenital Ulceration; studies on a Possible Mode of Action of Thalidomide, *British Journal of Dermatology*, vol./Iss:113, Supp. 28, pp. 141-144, Date: Jul. 1985.

Rao et al., Structural Specificity of Estrogens in the Induction of Mitotic Chromatid Non-Disjunction in Hela Cells, *Experimental Cell Research*, vol./Iss: 48, pp. 71-81, Date: 1967.

Rao et al., A Novel, Two-Step Synthesis of 2-Methoxyestradiol, *Synthesis*, pp. 168-169, Date: Mar. 1, 1977.

Ravindra, R., Effect of Estradiol on the in vitro Assembly of Rat Brain Tubulin, *Journal of Indian Institute of Science*, vol./Iss: 64 (3), pp. 27-35, Date: Mar. 1983.

Romanelli et al., Ethyl-p-Dimethylaminophenylacetate, *Organic Synthesis*, vol./Iss: 5, pp. 552, Date: Oct. 24, 1973.

Sakakibara et al., Effects of Diethylstilbestrol and its Methl Ethers on Aneuploidy Induction and Microtubule Distribution in Chinese Hamster V79 cells, *Mutation Research*, vol./Iss:263 (4), pp. 269-276, Date: Aug. 1991.

Sakakibara, Kyoichi, 2-Hydroxy-1,3,5(10)-estratriene derivatives (Abstract only) (Identifier: XP-002186126), *Chemical Abstracts*, vol./Iss:60(1), Date: Jan. 6, 1964.

Sato et al., Effect of Estradiol and Ethynylestradiol on Microtubule Distribution in Chinese Hamster V79 Cells, *Chemical and Pharmaceutical Bulletin*, vol./Iss: 40 (1), pp. 182-184, Date: Jan. 1992.

Sato et al., Disruptive Effect of Diethylstilbestrol on Microtubules, *Gann*, vol./Iss:75 (12), pp. 1046-1048, Date: Dec. 1984.

Sawada et al., Colchicine-Like Effect of Diethylstilbestrol (DES) on Mammalian Cells in Vitro, *Mutation Research*, vol./Iss: 57, pp. 175-182, Date: May 1978.

Schiff et al., Tubulin: A Target for Chemotherpeutic Agents, *Molecular Actions and Targets for Cancer Chemotherapeutic Agents*, pp. 483-507, Date: Jan. 1, 1981.

Seegers et al., Cyclic-AMP and Cyclic-GMP Production in MCF-7 Cells Exposed to Estradiol-17 Beta, Catecholestrogens and Methoxy-Estrogens in MCF-7 Cells (Meeting Abstract only), *Joint MCI-1st Symposium. Third 1st International Symposium. Biology and Therapy of Breast Cancer*, Date: Sep. 25, 1989.

Seegers, J.C. et al., The Cytotoxic Effects of Estradiol-17β Catecholestradiols and Methoxyestradiols on Dividing MCF-7 and HeLa Cells, *Journal of Steroid Biochemistry*, vol./Iss: 32 (6), pp. 797-809, Date: Jun. 1989.

Sharp et al., Diethylstilboestrol: the Binding and Effects of Diethylstilboestrol upon the Polymerisation and Depolymerisation of Purified Microtubule Protein in vitro, *Carcinogenesis*, vol./Iss: 6 (6), pp. 865-871, Date: Jun. 1985.

Shishkina et al., Synthesis and properties on condensed heterocyclic derivatives of estra-4, 9-dien-17.beta.-ol-3-one (Abstract only), *Khim.-Farm. Zh.*, vol./Iss: 8 (1), pp. 7-11, Date: 1974.

Sidky et al., Inhibition of Angiogenesis by Interferons: Effects on Tumor- and Lymphocyte-induced Vascular Responses, *Cancer Research*, vol./Iss: 47, pp. 5155-5161, Date: Oct. 1, 1987.

Siracusa et al., The Effect of Microtubule- and Microfilament-disrupting Drugs a Preimplantation Mouse Embryos (abstract Only), *Jouranl of Embryology and Experimental Morphology*, vol./Iss: 60, pp. 71-82, Date: Dec. 1980.

Spicer et al., Catecholestrogens Inhibit Proliferation and DNA Synthesis of Porcine Granulosa Cells in Vitro: Comparison with Estradiol, 5αdihydrotestosterone, Gonadotropins and Catecholamines (Chemical Abstracts Doc. No. 111:50609, 1989), *Molecular and Cellular Endocrinology*, vol./Iss: 64, pp. 119-126, Date: 1989.

Spyriounis et al., Copper (II) complex of an estradiol derivative with potent antiinflammatory properties (Abstract only), *Arch. Pharm.*, vol./Iss: 324 (9), pp. 533-536, Date: 1991.

Srivastava, A. et al., The Prognostic Significance of Tumor Vascularity in Intermediate-Thickness (0.76-4.0 mm Thick) Skin Melanoma, *American Journal of Pathology*, vol./Iss:133 (2), pp. 419-424, Date: Nov. 1988.

Staples et al., Structural Requirements for Steroid Inhibition of Sheep Lymphocyte Mitogenesis in vitro, *Steroids*, vol./Iss: 44 (5), pp. 419-433, Date: Nov. 1984.

Starkov et al., Mono- and Dialkylation of Guaiacol by Olefins on KU-2 Cation Exchanger (Abstract only), *Zhurnal Prikladnoj Khimii*, vol./Iss:41 (3), pp. 688-690, Date: 1968.

Sternlicht et al., Colchicine Inhibition of Microtubule Assembly via Copolymer Formation, *The Journal of Biological Chemistry*, vol./Iss:254 (20), pp. 10540-10550, Date: Oct. 25, 1979.

Sun et al., Antitumor Agents. 139. Synthesis and Biological Evaluation of Thiocolchicine Analogs 5,6-Dihydro -6($S$)-(acyloxy)-and 5,6-Dihydro-6($S$)-[(aroyloxy) methyl]-1,2,3- trimethoxy-9-(methylthio)-8$H$-cycloheptanaphthalen-8-ones as Novel Cytotoxic and Antimitotic Agents, *Journal of Medicinal Chemistry*, vol./Iss:36 (5), pp. 544-551, Date: Mar. 5, 1993.

Sunagawa et al., Synthesis of Colchicine; Synthesis of $d$Demethyoxydeoxy-hexahydrocolchicine, *Chemical & Pharmaceutical Bulletin*, vol./Iss: 9, pp. 81-83, Date: 1961.

Taylor, S. et al., Protamine is an Inhibitor of Angiogenesis, *Nature*, vol./Iss:297, pp. 307-312, Date: May 27, 1982.

Teranishi, M. et al., Methylation of Catechol Estrogen with Diazomethane, *Chemical and Pharmaceutical Bulletin*, vol./Iss:31 (9), pp. 3309-3314, Date: Sep. 1983.

Tsutsui et al., Comparison of Human Versus Syrian Hamster Cells in Culture for Induction of Mitotic Inhibition, Binucleation and Multinucleation, Following Treatment with Four Aneuploidogens, *Toxicology in Vitro*, vol./Iss:4 (1), pp. 75-84, Date: 1990.

Utne et al., The Synthesis of 2- and 4-Fluoroestradiol, *Journal of Organic Chemistry*, vol./Iss:33 (6), pp. 2469-2473, Date: Jun. 1968.

Van Geerestein et al., Structure of 11.beta.-(4-(dimethylamino)phenyl)-17.beta.-hydroxy-17. alpha.-(2-propenyl) estra-4,9-dien-3-one (Identifier only), *Acta Crystallogr., Sect. C: Cryst. Struct. Commun.*, vol./Iss:C43 (2), pp. 319-322, Date: 1987.

Van Tamelen et al., The Synthesis of Colchicine, *Tetrahedron*, vol./Iss:14 (1/2), pp. 8-34, Date: Sep. 1961.

Vicente et al., In Vitro Activity of Thalidomide Against Mycobacterium avium Complex, *Archives of Internal Medicine*, vol./Iss: 153 (4), pp. 534, Date: Feb. 22, 1993.

Wang et al., Photoaffinity Labeling of Human Placental Estradiol 17.beta.-dehydrogenase ith 2- And 4-azidoestrone, 2- and 4-azidoestradiol (abstract Only), *Shengwu Huaxue Zazhi*, vol./Iss:8 (6), pp. 715-718, Date: 1992.

Weidner, N. et al., Tumor angiogenesis: A New Significant and Independent Prognostic Indicator in Early-Stage Breast Carcinoma, *Journal of the National Cancer Institute*, vol./Iss: 84, pp. 1875-1887, Date: Dec. 16, 1992.

Weidner, N. et al., Tumor Angiogenesis Correlates with Metastasis in Invasive Prostate Carcinoma, *American Journal of Pathology*, vol./Iss:143 (2), pp. 401-409, Date: Aug. 1993.

Weidner, N. et al., Tumor Angiogenesis and Metastasis-Correlation in Invasive Breast Carcinoma, *New England Journal of Medicine*, vol./Iss:324 (1), pp. 1-8, Date: Jan. 3, 1991.

Welsch et al., Staphylostatic Activity of Some New Diphenols, Napthols, and Chalcones (Abstract only), *Experientia*, vol./Iss: 11, pp. 350-351, Date: 1955.

Wheeler et al., Mitotic Inhibition and Aneuploidy Induction by Naturally Occurring and Synthetic Estrogens in Chinese Hamster Cells in Vitro, *Mutation Research*, vol./Iss:171, pp. 31-41, Date: Jul. 1986.

Wheeler et al., Mitotic Inhibition and Chromosome Displacement Induced by Estradiol in Chinese Hamster Cells (Chemical Abstracts Doc. No. 105:54822, 1986), *Cell Motility and the Cytoskeleton*, vol./Iss: 7 (3), pp. 235-247, Date: 1987.

White et al., Treatment of Pulmonary Hemangiomatosis with Recombinant Interferon Alfa-2a, *The New England Journal of Medicine*, vol./Iss: 32 (18), pp. 1197-1200, Date: May 4, 1989.

Yasuda et al., Accelerated differentiation in seminiferous tubules of fetal mice prenatally exposed to ethinyl estradiol (Abstract only), *Anat. Embryol. (Berl.)*, vol./Iss:174 (3), pp. 289-299, Date: 1986.

Bacharach et al., In vivo Patterns of Expression of Urokinase and Its Inhibitor PAI-I Suggest a Concerted Role in Regulating Physiological Angiogenesis, *Procedings of the National Academy of Science USA*, vol./Iss:89 (22), pp. 10686-10690, Date: Nov. 15, 1992.

Baer et al., Corneal Laser Photocoagulation for Treatment of Neovascularization. Efficacy of 577 nm Yellow Dye Laser (Abstract only-Applicants do not have complete copy), *Ophthalmology*, vol./Iss:99 (2), pp. 173-179, Date: Feb. 1, 1992.

Boehme et al., Juxtapapillary Choroidal Neovascular Membrane in a Patient with Paget's Disease and Lattice Corneal Dystrophy (Abstract only-Applicants do not have complete copy), *Journal of the American Optometric Association*, vol./Iss:60 (8), pp. 612-616, Date: Aug. 1, 1989.

D'Amore et al., Mechanisms of Angiogenesis, *Annual Review of Physiology*, vol./Iss: 49, pp. 453-464, Date: Jan. 1, 1987.

Farmer et al., Retinal Vasculitis Associated with Autoantibodies to Sjogren's Syndrome A Antigen (Abstract only-Applicants do not have complete copy), *American Journal of Ophthalmology*, vol./Iss: 100 (6), pp. 814-821, Date: Dec. 1, 1985.

Gleichmann et al., Immunoblastic Lymphadenopathy, Systemic Lupus Erythematosus, and Related Disorders. Possible Pathogenetic Pathways. (Abstract only-Applicants do not have complete copy), *American Journal of Pathology*, vol./Iss:72 (4), pp. 708-723, Date: Oct. 1, 1979.

Hill et al., Pathogenesis of Pterygium (Abstract only-Applicants do not have complete copy), *Eye*, vol./Iss: 3 (Pt 2), pp. 218-226, Date: Jan. 1, 1990.

Hu et al., Interleukin-8 Stimulates Angiogenesis in Rats, *Inflammation*, vol./Iss: 17 (2), pp. 135-143, Date: Apr. 1, 1993.

Kahlon et al., Angiogenesis in Atherosclerosis (Abstract only-Applicants do not have complete copy), *Canadian Journal of Cardiology*, vol./Iss: 8 (1), pp. 60-64, Date: Jan. 1, 1992.

Kalina et al., Neovascularization of the Disc in Pars Planitis (Abstract only-Applicants do not have complete copy), *Retina*, vol./Iss: 10 (4), pp. 269-273, Date: Jan. 1, 1990.

Kornmehl et al., Bilateral Kerstitis in Lyme Diseases (Abstract only-Applicants do not have complete copy), *Ophthalmology*, vol./Iss:96 (8), pp. 1194-1197, Date: Aug. 1, 1989.

Lee et al., Inhibition of Growth and Angiogenesis of Human Neurofibrosarcoma by Heparin and Hydrocortisone (Abstract only-Applicants do not have complete copy), *Journal of Neurosurgery*, vol./Iss:73 (3), pp. 429-435, Date: Sep. 1, 1990.

Leveille et al., Platelet-Induced Retinal Neovascularization in Leukemia (Abstract only-Applicants do not have complete copy), *American Journal of Ophthalmology*, vol./Iss: 91 (5), pp. 640-644, Date: May 1, 1981.

Locci et al., Angiogenesis: A New Diagnostic Aspect of Obstetric and Gynecologic Echography, *Journal of Perinatal Medicine*, vol./Iss:21 (6), pp. 453-473, Date: Jan. 1, 1993.

Mahadevan et al., Metastasis and Angiogenesis, *Acta Oncologica*, vol./Iss: 29(1), pp. 97-103, Date: Jan. 1, 1990.

Nelson, J.D., Superior Limbic Keratoconjunctivitis (SLK) (Abstract only-Applicants do not have complete copy), *Eye*, vol./Iss:3 (Pt 2), pp. 180-189, Date: Jan. 1, 1989.

Numazawa et al., Synthesis of 2-Methoxy- and 4-Methoxy-Estrogens with Halogen-Methoxy Exchange Reactions *Journal of Chemical Research*, pp. 348-349, Date: Jan. 1, 1985.

Patz, A., Clinical and Experimental Studies on Retinal Neovascularization. XXXIX Edward Jackson Memorial Lecture. (Abstract only-Applicants do not have complete copy), *American Journal of Ophthalmology*, vol./Iss:94 (6), pp. 715-743, Date: Dec. 1, 1982.

Penfold et al., Age-Related Macular Degeneration: Ultrastructural Studies of the Relationship of Leucocytes to Angiogenesis (Abstract only-Applicants do not have complete copy), *Graefes Archive for Clinical and Experimental Ophthalmology*, vol./Iss:225 (1), pp. 70-76, Date: Jan. 1, 1987.

Penn et al., Variable Oxygen Exposure Causes Preretinal Neovascularization in the Newborn Rat, *Investigative Ophthalmology & Visual Science*, vol./Iss:34 (3), pp. 576-585, Date: Mar. 1, 1993.

Ribatti et al. Anti-Angiogenesis: A Multipurpose Therapeutic Tool?, *International Journal of Clinical & Laboratory Research*, vol./Iss: 23 (3), pp. 117-120, Date: Jan. 1, 1993.

Robinson et al., Retinal Vein Occlusion (Abstract only-Applicants do not have complete copy), *American Family Physician*, vol./Iss: 45 (6), pp. 2661-2666, Date: Jun. 1, 1992.

Rowsey et al., Radial Keratomy: Preliminary Report of Complications (Abstract only-Applicants do not have complete copy), *Ophthalmic Surgery*, vol./Iss: 13 (1), pp. 27-35, Date: Jan. 1, 1982.

Schaub et al., Novel Agents that Promote Bone Regeneration (Abstract only-Applicants do not have complete copy), *Current Opinion in Biotechnology*, vol./Iss:2 (6), pp. 868-871, Date: Dec. 1, 1991.

Servold, S.A., Growth Factor Impact on Wound Healing, *Clinics in Podiatric Medicine and Surgery*, vol./Iss:8 (4), pp. 937-953, Date: Oct. 1, 1991.

Sheela et al., Angiogenic and Invasive Properties of Neurofibroma Schwann Cells, *Journal of Cell Biology*, vol./Iss:111 (2), pp. 645-653, Date: Aug. 1, 1990.

Shweiki et al., Patterns of Expression of Vascular Endothelial Growth Factor (VEGF) and VEGF Receptors in Mice Suggest a Role in Hormonally Regulated Angiogenesis (Abstract only-Applicants do not have complete copy), *Journal of Clinical Investigation*, vol./Iss:91 (5), pp. 2235-2243, Date: May 1, 1993.

Tabbara, K.F., Disruption of the Choroidoretinal Interface by Toxoplasma (Abstract only-Applicants do not have complete copy), *Eye*, vol./Iss:4 (Part 2), pp. 366-373, Date: Jan. 1, 1990.

Wiedemann, P., Growth Factors in Retinal Disease: Proliferative Vitreoretinopathy, Proliferative Diabetic Retinopathy, and Retinal Degeneration (Abstract only-Applicants do not have complete copy), *Survey of Ophthalmology*, vol./Iss:36 (5), pp. 373-384, Date: Mar. 1, 1992.

* cited by examiner

ESTROGENIC COMPOUNDS AS ANTI-MITOTIC AGENTS

CROSS-REFERENCE TO RELATED APPLICATIONS

This application is a continuation of application Ser. No. 09/780,650, filed Feb. 12, 2001, now U.S. Pat. No. 7,109,187, which is a continuation of application Ser. No. 09/436,610, filed on Nov. 9, 1999, now abandoned, which is a continuation of application Ser. No. 09/243,158, filed Feb. 2, 1999, now U.S. Pat. No. 6,528,676, which is a division of application Ser. No. 08/838,699, filed Apr. 25, 1997, now U.S. Pat. No. 5,892,069, which is a division of application Ser. No. 08/571,265, filed Dec. 12, 1995, now U.S. Pat. No. 5,661,143, which is a continuation of application Ser. No. 08/102,767, filed Aug. 6, 1993, now U.S. Pat. No. 5,504,074.

BACKGROUND OF THE INVENTION

This invention relates to treating disease states characterized by abnormal cell mitosis.

Cell mitosis is a multi-step process that includes cell division and replication (Alberts, B. et al. In *The Cell*, pp. 652-661 (1989); Stryer, E. *Biochemistry* (1988)). Mitosis is characterized by the intracellular movement and segregation of organelles, including mitotic spindles and chromosomes. Organelle movement and segregation are facilitated by the polymerization of the cell protein tubulin. Microtubules are formed from $\alpha$ and $\beta$ tubulin polymerization and the hydrolysis of GTP. Microtubule formation is important for cell mitosis, cell locomotion, and the movement of highly specialized cell structures such as cilia and flagella.

Microtubules are extremely labile structures that are sensitive to a variety of chemically unrelated anti-mitotic drugs. For example, colchicine and nocadazole are anti-mitotic drugs that bind tubulin and inhibit tubulin polymerization (Stryer, E. *Biochemistry* (1988)). When used alone or in combination with other therapeutic drugs, colchicine may be used to treat cancer (WO-9303729-A, published Mar. 4, 1993; J03240726-A, published Oct. 28, 1991), alter neuromuscular function, change blood pressure, increase sensitivity to compounds affecting sympathetic neuron function, depress respiration, and relieve gout (*Physician's Desk Reference*, Vol. 47, p. 1487, (1993)).

Estradiol and estradiol metabolites such as 2-methoxyestradiol have been reported to inhibit cell division (Seegers, J. C. et al. *J. Steroid Biochem.* 32, 797-809 (1989); Lottering, M-L. et al. *Cancer Res.* 52, 5926-5923 (1992); Spicer, L. J. and Hammond, J. M. *Mol. and Cell. Endo.* 64, 119-126 (1989); Rao, P. N. and Engelberg, *J. Exp. Cell Res.* 48, 71-81 (1967)). However, the activity is variable and depends on a number of in vitro conditions. For example, estradiol inhibits cell division and tubulin polymerization in some in vitro settings (Spicer, L. J. and Hammond, J. M. *Mol. and Cell. Endo.* 64, 119-126 (1989); Ravindra, R., *J. Indian Sci.* 64(c) (1983)), but not in others (Lottering, M-L. et al. *Cancer Res.* 52, 5926-5923 (1992); Ravindra, R., *J. Indian Sci.* 64(c) (1983)). Estradiol metabolites such as 2-methoxyestradiol will inhibit cell division in selected in vitro settings depending on whether the cell culture additive phenol red is present and to what extent cells have been exposed to estrogen. (Seegers, J. C. et al. Joint NCI-IST Symposium. Biology and Therapy of Breast Cancer. 9/25-9/27, 1989, Genoa, Italy, Abstract A58).

Numerous diseases are characterized by abnormal cell mitosis. For example, uncontrolled cell mitosis is a hallmark of cancer. In addition, cell mitosis is important for the normal development of the embryo, formation of the corpus luteum, wound healing, inflammatory and immune responses, angiogenesis and angiogenesis related diseases.

SUMMARY OF THE INVENTION

I have discovered that certain compounds within the scope of the general formulae set forth below in the claims are useful for treating mammalian diseases characterized by undesired cell mitosis. Without wishing to bind myself to any particular theory, such compounds generally inhibit microtuble formation and tubulin polymerization and/or depolymerization. Compounds within the general formulae having said inhibiting activity are preferred. Preferred compositions may also exhibit a change (increase or decrease) in estrogen receptor binding, improved absorbtion, transport (e.g. through blood-brain barrier and cellular membranes), biological stability, or decreased toxicity. I have also discovered certain compounds useful in the method, as described by the general formulae of the claims.

A mammalian disease characterized by undesirable cell mitosis, as defined herein, includes but is not limited to excessive or abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neovascular glaucoma and Osler Weber syndrome. Other undesired angiogenesis involves normal processes including ovulation and implantation of a blastula. Accordingly, the compositions described above can be used to block ovulation and implantation of a blastula or to block menstruation (induce amenorrhea).

The bond indicated by C . . . C is absent or, in combination with the C—C bond is the unit HC=CH.

Other features and advantages of the invention will be apparent from the following description of preferred embodiments thereof.

DESCRIPTION OF THE PREFERRED EMBODIMENTS

COMPOUNDS ACCORDING TO THE INVENTION

As described below, compounds that are useful in accordance with the invention include novel estradiol derivatives that bind tubulin, inhibit microtubule formation or exhibit anti-mitotic properties. Specific compounds according to the invention are described below. Those skilled in the art will appreciate that the invention extends to other compounds within the formulae given in the claims below, having the described characteristics. These characteristics can be determined for each test compound using the assays detailed below and elsewhere in the literature.

Figure 3:
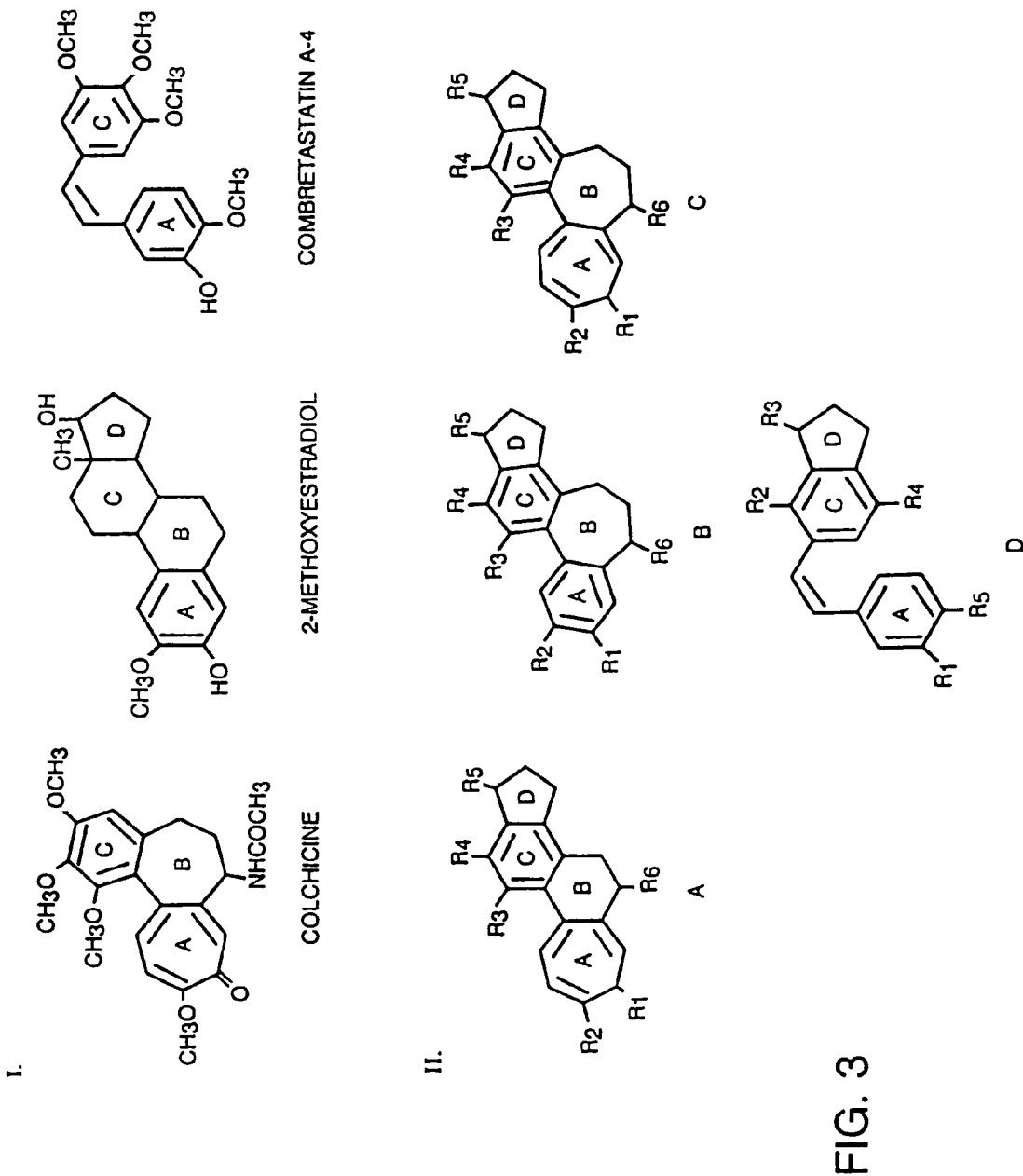
FIG. 3 depicts: I. colchicine, 2-methoxyestradiol and combretastatin A-4, and II. various estradiol derivatives comprising colchicine (a-c) or combretastatin A-4 (d) structural motifs as described below.

Without wishing to bind myself to specific mechanisms or theory, it appears that certain compounds that are known to inhibit microtubule formation, bind tubulin and exhibit anti-mitotic properties such as colchicine and combretastatin A-4 share certain structural similarities with estradiol. FIG. 3 illustrates the molecular formulae of estradiol, colchicine, combretastatin A-4, and improved estradiol derivatives that bind tubulin inhibit microtubule assembly and exhibit anti-mitotic properties. Molecular formulae are drawn and oriented to emphasize structural similarities between the ring structures of colchicine, combretastatin A-4, estradiol, and certain estradiol derivatives. Estradiol derivatives are made by incorporating colchicine or combretastatin A-4 structural motifs into the steroidal backbone of estradiol.

FIG. 3, part I, depicts the chemical formulae of colchicine, 2-methoxyestradiol and combretastatin A-4. FIG. 3, part IIa-d, illustrates estradiol derivatives that comprise structural motifs found in colchicine or combretastatin A-4. For example, part II a-c shows estradiol derivatives with an A and/or B ring expanded from six to seven carbons as found in colchicine and part IId depicts an estradiol derivative with a partial B ring as found in combretastatin A-4. Each C ring of an estradiol derivative, including those shown in FIG. 3, may be fully saturated as found in 2-methoxyestradiol. $R_{1-6}$ represent a subset of the substitution groups found in the claims. Each $R_1 \rightarrow R_6$ can independently be defined as $-R_1$, $OR_1$, $-OCOR_1$ $-SR_1$, $-F$, $-NHR_2$, $-Br$, $-I$, or $-C\equiv CH$.

Anti-Mitotic Activity In Situ

Anti-mitotic activity is evaluated in situ by testing the ability of an improved estradiol derivative to inhibit the proliferation of new blood vessel cells (angiogenesis). A suitable assay is the chick embryo chorioallantoic membrane (CAM) assay described by Crum et al. *Science* 230:1375 (1985). See also, U.S. Pat. No. 5,001,116, hereby incorporated by reference, which describes the CAM assay. Briefly, fertilized chick embryos are removed from their shell on day 3 or 4, and a methylcellulose disc containing the drug is implanted on the chorioallantoic membrane. The embryos are examined 48 hours later and, if a clear avascular zone appears around the methylcellulose disc, the diameter of that zone is measured. Using this assay, a 100 mg disk of the estradiol derivative 2-methoxyestradiol was found to inhibit cell mitosis and the growth of new blood vessels after 48 hours. This result indicates that the anti-mitotic action of 2-methoxyestradiol can inhibit cell mitosis and angiogenesis.

Anti-Mitotic Activity In Vitro

Anti-mitotic activity can be evaluated by testing the ability of an estradiol derivative to inhibit tubulin polymerization and microtubule assembly in vitro. Microtubule assembly is followed in a Gilford recording spectrophotometer (model 250 or 2400S) equipped with electronic temperature controllers. A reaction mixture (all concentrations refer to a final reaction volume of 0.25 μl) contains 1.0M monosodium glutamate (ph 6.6), 11.0 mg/ml (10 μM) tubulin, 1.0 mM $MgCl_2$, 4% (v/v) dimethylsulfoxide and 20-75 μM of a composition to be tested. The 0.24 ml reaction mixtures are incubated for 15 min. at 37° C. and then chilled on ice. After addition of 10 μl 2.5 mM GTP, the reaction mixture is transferred to a cuvette at 0° C., and a baseline established. At time zero, the temperature controller of the spectrophotometer is set at 37° C. Microtubule assembly is evaluated by increased turbity at 350 mm. Alternatively, inhibition of microtubule assembly can be followed by transmission electron microscopy as described in Example 2 below.

Indications

The invention can be used to treat any disease characterized by abnormal cell mitosis. Such diseases include, but are not limited to: abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neuroscular glacoma and Oster Webber syndrome.

Improved Estradiol Derivative Synthesis

Known compounds that are used in accordance with the invention and precursors to novel compounds according to the invention can be purchased, e.g., from Sigma Chemical Co., St. Louis, Steroloids and Research Plus. Other compounds according to the invention can be synthesized according to known methods from publicly available precursors.

The chemical synthesis of estradiol has been described (Eder, V. et al., *Ber* 109, 2948 (1976); Oppolzer, D. A. and Roberts, D. A. *Helv, Chim. Acta.* 63, 1703, (1980)). Synthetic methods for making seven-membered rings in multicyclic compounds are known (Nakamuru, T. et al. *Chem. Pharm. Bull.* 10, 281 (1962); Sunagawa, G. et al. *Chem. Pharm. Bull.* 9, 81 (1961); Van Tamelen, E. E. et al. *Tetrahedran* 14, 8-34 (1961); Evans, D. E. et al. *JACS* 103, 5813 (1981)). Those skilled in the art will appreciate that the chemical synthesis of estradiol can be modified to include 7-membered rings by making appropriate changes to the starting materials, so that ring closure yields seven-membered rings. Estradiol or estradiol derivatives can be modified to include appropriate chemical side groups according to the invention by known chemical methods (*The Merck Index*, 11th Ed., Merck & Co., Inc., Rahway, N.J. USA (1989), pp. 583-584).

Administration

The compositions described above can be provided as physiologically acceptable formulations using known techniques, and these formulations can be administered by standard routes. In general, the combinations may be administered by the topical, oral, rectal or parenteral (e.g., intravenous, subcutaneous or intramuscular) route. In addition, the combinations may be incorporated into biodegradable polymers allowing for sustained release, the polymers being implanted in the vicinity of where delivery is desired, for example, at the site of a tumor. The biodegradable polymers and their use are described in detail in Brem et al., *J. Neurosurg.* 74:441-446 (1991).

The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01-1 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tables may be made by molding, in a suitable machine, a mixture of the powdered compound moistened with an inert liquid diluent. The tablets may optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of this invention may include other agents convention in the art having regard to the type of formulation in question, for example, those suitable for oral administration may include flavoring agents.

EXAMPLE 1

Figure 1:
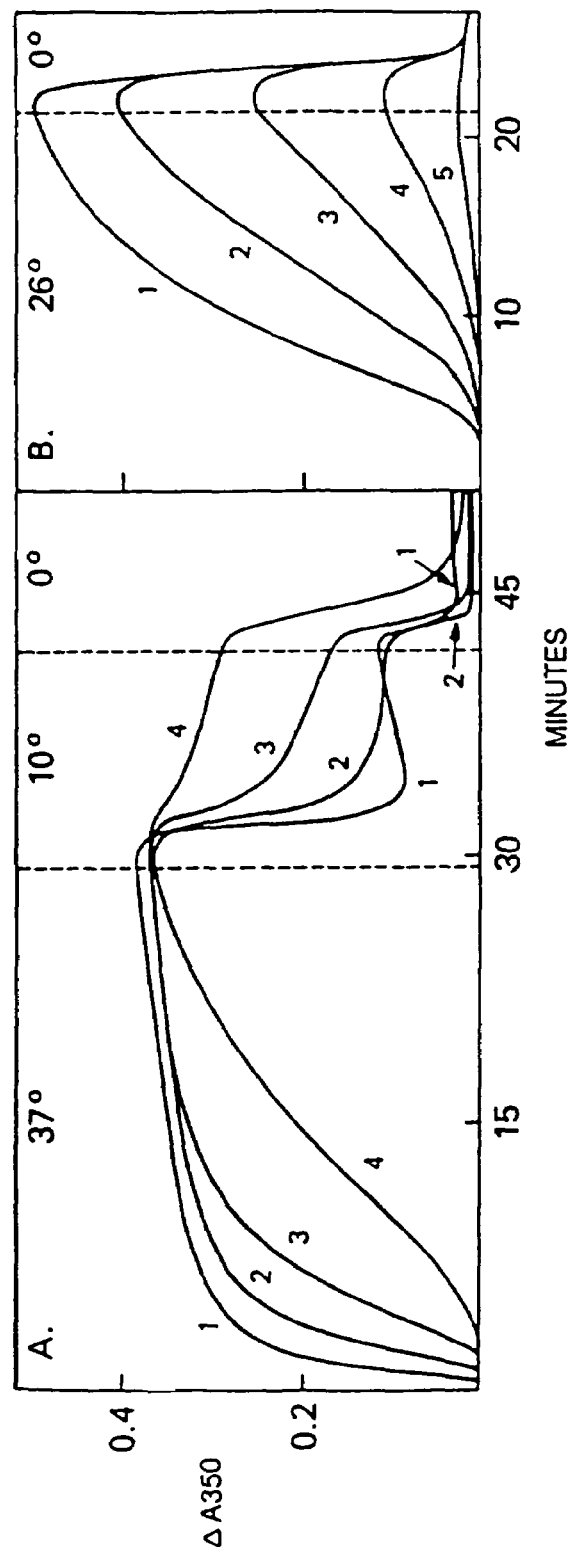
FIG. 1 is a graph illustrating the inhibition of tubulin polymerization by 2-methoxyestradiol described by Example 1 below.

FIG. 1 illustrates the inhibition of tubulin polymerization by 2-methoxyestradiol.

A. Each reaction mixture (all concentrations refer to the final reaction volume of 0.25 ml) contained 1.0 M monosodium glutamate (pH 6.6), 1.0 mg/ml (10 µM) tubulin, 1.0 mM $MGCl_2$, 4% (v/v) dimethylsulfoxide, and either 0 (curve 1), 20 µM (curve 2), 40 µM (curve 3), or 75 µM (curve 4) 2-methoxyestradiol. The 0.24 ml reaction mixtures were incubated for 15 min at 37° C. and chilled on ice. After addition of 10 µl of 2.5 mM GTP the reaction mixtures were transferred to cuvettes held at 0° C., and baselines were established. At time zero the temperature controller was set at 37 C. At the times indicated by the vertical dashed lines the temperature controller was set at the indicated temperatures.

B. Each reaction mixture contained 0.8 M monosodium glutamate (pH 6.6), 1.2 mg/ml (12 µM) tubulin, 4% (v/v) dimethylsulfoxide, and either 0 (curve 1), 1.0 µM (curve 2), 2.0 µM (curve 3), 3.0 µM (curve 4), or 4.0 µM (curve 5) 2-methoxyestradiol. The 0.24 ml reaction mixtures were incubated for 15 min at 26° C. and chilled on ice. After addition of 10 µl of 10 mM GTP the reaction mixtures were transferred to cuvettes held at 0° C., and baselines were established. At time zero the temperature controller was set at 26° C. At the time indicated by vertical dashed line the temperature controller was set at 0° C.

EXAMPLE 2

Transmission electron microscopy (TEM) can show differences between the morphology of polymerized tubulin formed in the absence or presence of 2-methoxyestradiol. After a 30 min incubation (37° C.) of reaction mixtures containing the components described in Example 1, 75 µM 2-methoxyestradiol was added, and aliquot's were placed on 200-mesh carbon coated copper grids and stained with 0.5%

(w/v) uranyl acetate. TEM magnifications from 23,100× to 115,400× were used to visualize differences in tubulin morphology.

EXAMPLE 3

Figure 2:
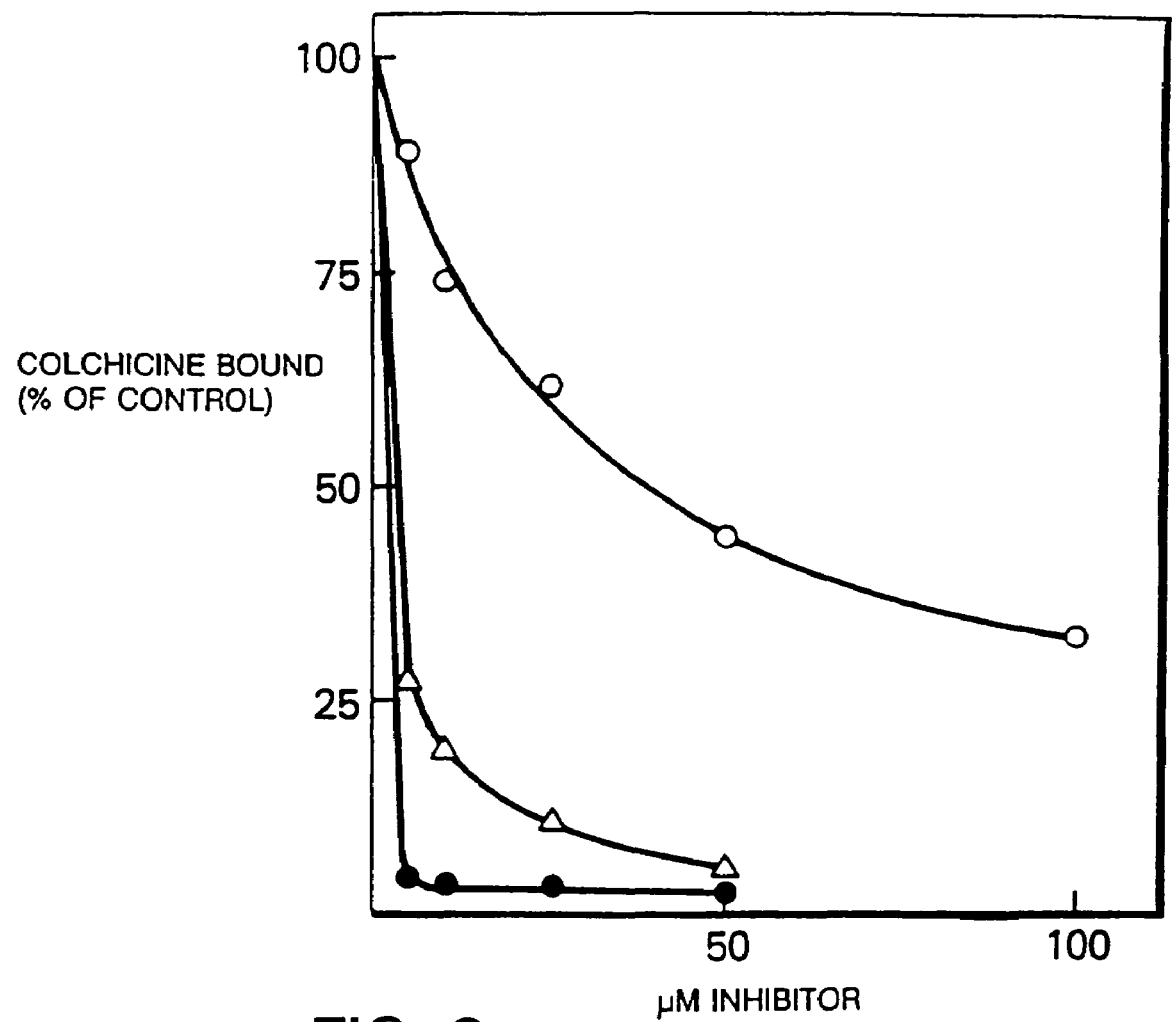
FIG. 2 is a graph illustrating the inhibition of colchicine binding to tubulin by 2-methoxyestradiol described by Example 2 below.

FIG. 2 illustrates that 2-methoxyestradiol inhibits colchicine binding to tubulin. Reaction conditions were as described in the text, with each reaction mixture containing 1.0 μM tubulin, 5% (v/v) dimethyl sulfoxide, 5 μM [$^3$H] colchicine, and inhibitor at the indicated concentrations. Incubation was for 10 min at 37° C. Symbols as follows: ○, 2-methoxyestradiol; ●, combretastatin A-4; Δ, dihydrocombretastatin A-4. Combretastatin A-4 and dihydrocombretastatin A-4 are compounds with anti-mitotic activity similar to colchicine.

EXAMPLE 4

Table 1 illustrates the inhibitory effects on tubulin polymerization in vitro exhibited by estradiol or estradiol derivatives, plant anti-mitotic compounds such as colchicine, combretastatin A-4 or other plant compounds. The method is given in Example 1.

EXAMPLE 5

Table 2 lists estrogens, estradiol or estradiol derivatives that inhibit colchicine binding to tubulin, by the method given in Example 3.

TABLE 1

| Estrogenic Compound | IC$_{50}$ (μM ± S.D.) |
| --- | --- |
| 2-Methoxyestradiol | 1.9 ± 0.2 |
| Diethylstilbestrol | 2.4 ± 0.4 |
| 2-Bromoestradiol | 4.5 ± 0.6 |
| 2-Methoxyestrone | 8.8 ± 1 |
| 17-Ethynylestradiol | 10.0 ± 2 |
| 2-Fluoroestradiol | 27.0 ± 6 |
| Estradiol | 30.0 ± 6 |
| Estrone | >40 |
| 2-Methoxy-17-ethynylestradiol | >40 |
| Estriol | >40 |
| 2-Methoxyestriol | >40 |
| Estradiol-3-O-methyl ether | >40 |
| 2-Methoxyestradiol-3-O-methyl ether | >40 |
| 4-Methoxyestradiol | >40 |
| 4-Methoxyestradiol-3-O-methyl ether | >40 |
| Plant Products | |
| Colchicine | 0.80 ± 0.07 |
| Podophyllotoxin | 0.46 ± 0.02 |
| Combretastatin A-4 | 0.53 ± 0.05 |
| Dihydrocombretastatin A-4 | 0.63 ± 0.03 |

IC$_{50}$ values are defined as the concentration of an estradiol derivative required to inhibit tubulin polymerization by 50%. IC$_{50}$ values were obtained in at least two independent experiments for non-inhibitory agents (IC$_{50}$>40 μM) and at least three independent experiments for inhibitory compounds. IC$_{50}$ values were obtained graphically, and average values are presented. S.D., standard deviation.

TABLE 2

| Estrogenic Compound | Percent inhibition ± S.D. |
| --- | --- |
| 2-Methoxyestradiol | 82 ± 2 |
| 2-Methoxyestrone | 57 ± 6 |
| 17-Ethynylestradiol | 50 ± 7 |
| Estradiol | 38 ± 4 |
| Diethylstilbestrol | 30 ± 4 |

Reaction conditions were described in Example 3, with each reaction mixture containing 1.0 μM tubulin, 5% (v/v) dimethyl sulfoxide, 2 μM [$^3$H]colchicine, and 100 μM inhibitor. Incubation was for 10 min at 37° C. Average values obtained in three independent experiments are presented in the table, except for 2-methoxyestrone, which was only examined twice. S.D., standard deviation.

What is claimed is:

1. A method for treating tumor metastasis in a human or an animal comprising administering to the human or animal a composition comprising an effective angiogenesis-inhibiting amount of a composition comprising 2-methoxyestradiol, wherein said composition is in the form of a suspension.

2. The method of claim 1, wherein said composition further comprises a suspending agent.

3. The method of claim 1, wherein said composition further comprises a surface active agent.

4. The method of claim 1, wherein said effective angiogenesis-inhibiting amount is 0.01 to 100 mg/kg/day.

5. The method of claim 2, wherein said effective angiogenesis-inhibiting amount is 0.01 to 100 mg/kg/day.

6. The method of claim 3, wherein said effective angiogenesis-inhibiting amount is 0.01 to 100 mg/kg/day.

7. The method of claim 1, wherein said suspension is in an aqueous liquid.

8. The method of claim 2, wherein said suspension is in an aqueous liquid.

9. The method of claim 3, wherein said suspension is in an aqueous liquid.

10. The method of claim 4, wherein said suspension is in an aqueous liquid.

11. A method for treating tumor metastasis in a human or an animal comprising administering to the human or animal a composition comprising an effective angiogenesis-inhibiting amount of a composition comprising 2-methoxyestradiol and a surface active agent.

12. The method of claim 11, wherein said composition is administered orally.

* * * * *